(12) United States Patent
Hu et al.

(10) Patent No.: US 6,194,403 B1
(45) Date of Patent: Feb. 27, 2001

(54) TACRINE DERIVATIVES FOR TREATING ALZHEIMER'S DISEASE

(75) Inventors: Ming-Kuan Hu, Taipei (TW); Jiajiu Shaw, Ann Arbor, MI (US)

(73) Assignee: Unitech Pharmaceuticals, Inc., Ann Arbor, MI (US)

( * ) Notice: Subject to any disclaimer, the term of this patent is extended or adjusted under 35 U.S.C. 154(b) by 0 days.

(21) Appl. No.: 09/392,485

(22) Filed: Sep. 9, 1999

(51) Int. Cl.[7] .................. C07D 471/04; C07D 219/12; A61K 31/4375; A61K 31/44; A61K 31/55
(52) U.S. Cl. .................. 514/213.01; 514/297; 546/106
(58) Field of Search .................. 514/297, 213.01; 546/106

(56) References Cited

U.S. PATENT DOCUMENTS 5,783,584 * 7/1998 Pang et al. .................. 514/297

* cited by examiner

*Primary Examiner*—Alan L. Rotman
(74) *Attorney, Agent, or Firm*—Brinks Hofer Gilson & Lione

(57) ABSTRACT

A series of tacrine derivatives has be synthesized and disclosed. These tacrine derivatives were claimed to be new and be useful for the treatment of Alzheimer's disease alone or in combination with other drugs for Alzheimer's disease. These tacrine derivatives may be formulated into suitable pharmaceutical dosage forms for the treatment of Alzheimer's disease.

8 Claims, 1 Drawing Sheet

Tacrine (1a), X = H
6-Chlorotacrine (1b), X = Cl

Bis-tacrines 2a, n = 7
2b, n = 8

Chemical structures of tacrine derivatives

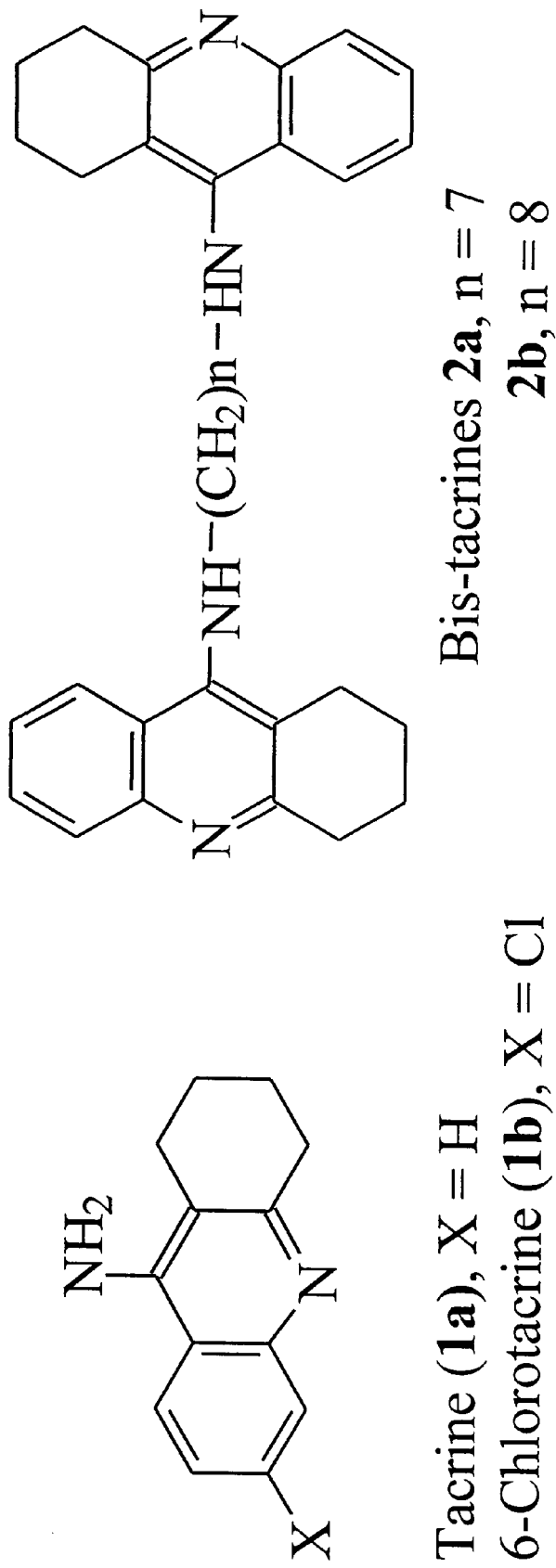
FIG. 1 Chemical structures of tacrine derivatives

TACRINE DERIVATIVES FOR TREATING ALZHEIMER'S DISEASE

FIELD OF INVENTION

This invention relates to the syntheses of a series of tacrine derivatives and the methods of treating Alzheimer's disease by these tacrine derivatives.

BACKGROUND OF THE INVENTION

Alzheimer's disease is critical and may be life threatening for human beings, especially for older people. Demographic data indicate that the percentage of elderly in the population is increasing. Therefore, the threat of Alzheimer's disease is greater and greater. Although there is not a real cure for this disease, there are several drugs for treating Alzheimer's disease, such as tacrine (Parke-Davis), Aricett (Pfizer-Eisai), and Excelon (Novartis).

Tacrine (Tetrahydroaminoacridine or THA, FIG. 1 1a) functions as the acetylcholinesterase (AChE) inhibitor and was approved by the U.S. Food and Drug Administration (FDA) for treating Alzheimer's disease in recent year. It is marketed as Cognex® by Parke-Davis. (Crimson, M. L. Ann. Pharmacother. 1994, 28, 744–751). However, there is considerable debate over some drawbacks of tacrine due to its many actions in the CNS and its serious toxicity (Watkins, P. B. et al., J. Am. Med. Assoc. 1994, 271, 992–998).

Therefore, it is very important to design and develop a more selective inhibitor of AChE as opposed to tacrine. Recently, tacrin-1-ol (velnacrine), one of the major metabolites of tacrine, was chosen for clinical trials in Alzheimer's disease (Puri, S. K. et al., J. Clin. Pharmacol. 1990, 30, 948–955). A series of substituted tacrin-1-ols were also developed and found to show more potent anti-AChE activities than did tacrine (Shutske, G. M. et al., J Med. Chem. 1989, 32, 1805–1813). 6-Chloro-tacrin-1-ol was reported to be almost 30 times as potent as tacrine and 6-fluoro-tacrin-1-ol was reported to be slightly more potent than tacrine. Another report revealed that 6-chlorotacrine (1b, FIG. 1) exhibited stronger binding strength toward AChE than did tacrine (Wlodek S. T. et al., Biopolymers 1996, 38, 109–117). In addition to the above monomeric derivatives of tacrine, Pang and coworkers disclosed a series of bis-tacrines as highly potent and selective inhibitors (2a,b) of AChE (Pang, Y. P. et al., J. Biol. Chem. 1996, 271, 23646–23649). These bis-tacrines were up to 10,000-fold more selective and 1,000-fold more potent than tacrine in inhibiting rat AChE.

All these studies indicate that tacrine may be improved for it selectivity and potency. Based on the above findings, we are disclosing a series of innovative tacrine derivatives for the treatment of Alzheimer's disease.

BRIEF SUMMARY OF THE INVENTION

This invention discloses a series of tacrine derivatives for the treatment of Alzheimer's disease. Examples comprise chloro-substituted bis-tacrines and chloro-substituted tacrine derivatives. Based on the above references, these tacrine derivatives should have very good potential for treating Alzheimer's disease. To the best of our knowledge, none of the above references disclose a tacrine derivative that is the same as the tacrine derivatives disclosed in this invention.

BRIEF DESCRIPTION OF THE DRAWING

The following drawing forms part of the present specification and is included to further demonstrate certain aspects of the present invention. The invention may be better understood by reference to this drawing in combination with the detailed description of specific embodiments presented herein.

FIG. 1. Chemical Structures of tacrine derivatives

DETAILED DESCRIPTION OF THE INVENTION

Tacrine (1a) (Tetrahydroaminoacrdine or THA) functions as the acetylcholinesterase (AChE) inhibitor. It was approved by the U.S. Food and Drug Administration (FDA) for treating Alzheimer's disease several years ago. However, it has been reported that tacrine has serious side effect and the patients need to be carefully monitored while being treated by tacrine.

Many derivatives of tacrine were made in order to reduce the side effects or increase the potency of tacrine. Most notable examples include 6-chlorotacrine (1b, FIG. 1) which exhibited stronger binding strength toward AChE than did tacrine (Wlodek S. T. et al., Biopolymers 1996, 38, 109–117). Recently, a series of bis-tacrines were shown to be highly potent and selective inhibitors of AChE (2a and 2b in FIG. 1; Pang, Y. P. et al., J. Biol. Chem. 1996, 271, 23646–23649). These analogs were up to 10,000-fold more selective and 1,000-fold more potent than tacrine in inhibiting rat AChE.

This invention discloses a series of rationally designed chloro-substituted bis-tacrines which are different from previous arts. In one example, a chloride is attached at 6-position of a bis-tacrinyl moiety (see Scheme 1). These substituted bis-tacrine derivatives of tacrine should be highly potent and selective against AChE based on the results and reports referenced in "BACKGROUND".

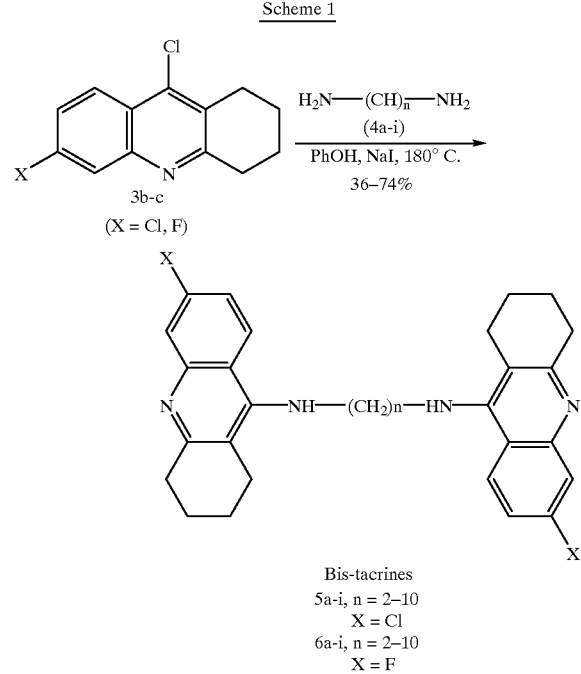

Scheme 1

It has been reported that most alkyl derivatives of 6-chloro-9-alkylaminotetrahydroacridines can be made by reacting 6,9-dichlorotetrahydroacridine (3b) with appropriate amines (Sargent, L. J. and Small, L. J Org. Chem. 1947, 12, 571–576). A modified fashion was therefore optimized here to efficiently prepare the series of bis-chlorotacrine derivatives as shown Scheme 1. Heating the mixture of 3b (or 3c) and a series of 1,n-diaminoalkanes (4a–i, 0.5 equiv.) respectively in the presence of phenol and catalytic amounts of sodium iodide at 180° C. for 2 h furnished 1,n-bis-chlorotacrinyl alkanes (5a–i or 6a–i) in 36–56% yield after purification from silica gel chromatography. Under similar condition, direct reaction of 3a–c with 4k provided 7a–c (Scheme 2). Under similar conditions, direct reaction of 3b–c and tryptamine provided N-[2-(3-indolyl)ethyl]-6-chlorotacrine (8a–c) in 65% yield (Scheme 3).

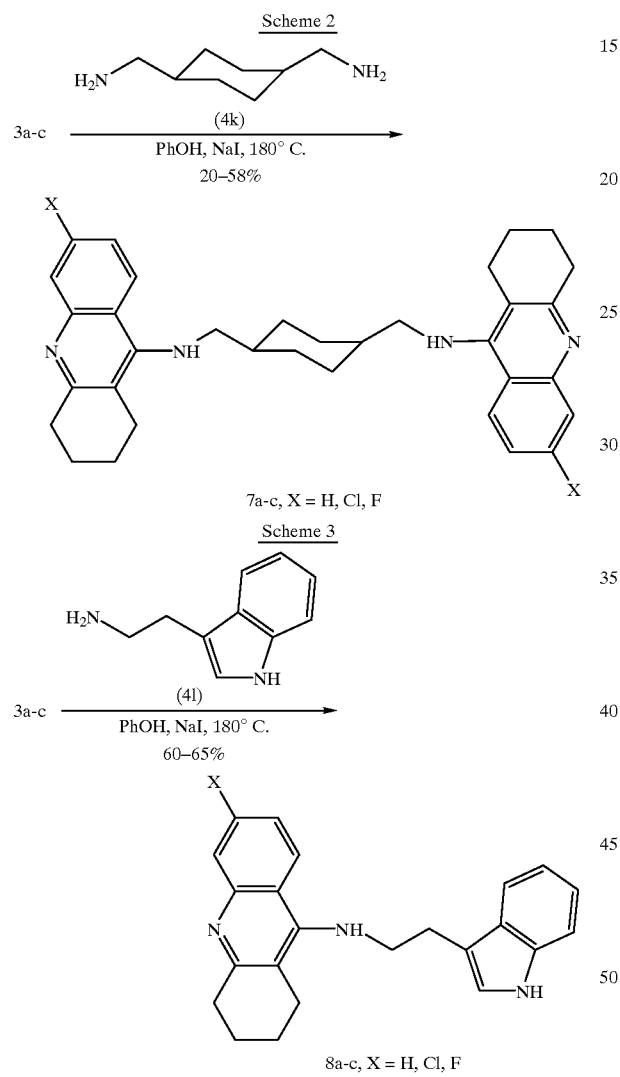

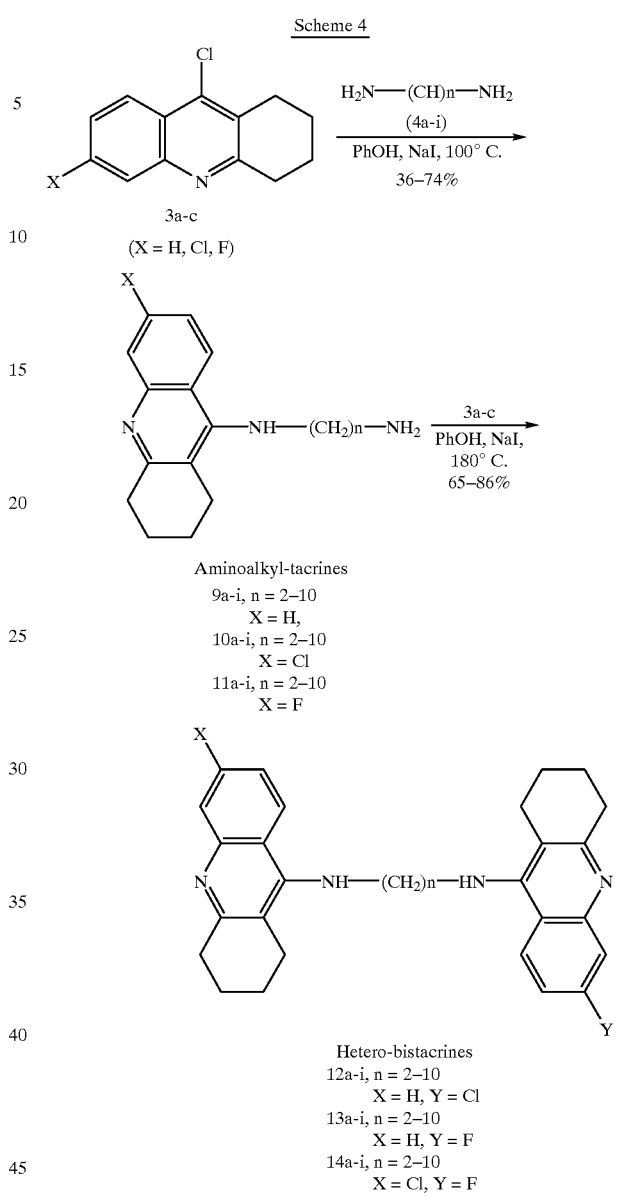

Yet another type of bistacrine derivatives disclosed in this invention may be synthesized and the reaction is shown in Scheme 4. In the reaction, compound 3a–c is reacted with 4a–i under PhOH, NaI at 100° C. to first form aminoalkyl-tacrines (9a–i, 10a–i, or 11a–i). The aminoalkyl-tacrine is then reacted with 3a–c in the presence of PhOH and NaI at 180° C. to form a hetero-bistacrins (12a–i, 13a–i, 14a–i) where the substituted groups on the two heterocyclic rings are different.

Experimental

All reagents were commercial materials and were used directly unless otherwise noted. Melting points were recorded on a Thomas Hoover capillary melting point apparatus in open capillary tubes and are uncorrected. NMR spectra were recorded on a Varian Gemini at 300 MHz for $^1$H and 75 MHz for $^{13}$C, the chemical shifts are reported in δ values and the coupling constants (J) were measured in Hz. Elemental analyses were determined using a Perkin-Elmer 240 EA analyzer. Optical rotations were recorded with a Perkin-Elmer 241 automatic polarimeter. Chromatography refers to flash chromatography on silica gel (silica gel 60, 230–400 mesh ASTM, E. Merck). Reaction products were visualized by WV-fluorescence (254 mm).

EXAMPLE 1

6,9-Dichloro- 1,2,3,4-tetrahydroacridine (3b)

To a mixture of 4-chloroanthranilic acid (8.58 g, 50.0 mmol) and cyclohexanone (5.18 mL, 50.0 mmol) was added carefully with 20 mL of phosphorus oxychloride at ice bath. The resulting mixture was heated under reflux for 2 hours. The mixture was cooled at room temperature and concentrated and then diluted with $CHCl_3$. The resulting mixture was poured into a mixture of crashed ice and aqueous $K_2CO_3$ solution. The organic layer was washed with saturated brine, dried over anhydrous $K_2CO_3$ and concentrated in vacuo to give 12.6 g (99%) of a yellow solid. A small portion of the solid was recrystallized with acetone for characterization: mp 85–87° C. (lit. 86.5–87° C.); $^1H$ NMR (300 MHz, $CDCl_3$) 8.88 (s, 1H, Ar—H), 8.27 (dd, J=7.1, 1.4 Hz, 1H, Ar—H), 7.74 (dd, J=7.1, 1.9 Hz, 1H, Ar—H), 3.64 (s br, 2H, $CH_2$), 3.09 (s br, 2H, $CH_2$), 2.02 (s br, 4H, $CH_2CH_2$); $^{13}C$-NMR (75 MHz, $CDCl_3$)159.1, 150.9, 141.4, 138.2, 131.7, 131.5, 1264, 121.6, 30.0, 27.5, 21.9, 21.1; EIMS: 255 ($M+4^+$, 13), 253 ($M+2^+$, 66), 251 ($M^+$, 100), 218 ($M-HCl+2^+$, 20), 216 ($M-HCl^+$, 60), HR-EIMS: exact calc'd for $C_{13}H_{11}NCl_2$ $[M]^+$251.0271, found 251.0277.

EXAMPLE 2

6-Chloro-9-fluoro-1,2,3,4-tetrahydroacridine (3c)

To a mixture of 4-fluoroanthranilic acid (3.00 g, 19.6 mmol) and cyclohexanone (2.05 mL, 19.6 mmol) was added carefully with 10 mL of phosphorus oxychloride at ice bath and the mixture was carefully heated under reflux for 2 h. The mixture was then cooled at room temperature and concentrated and diluted with $CHCl_3$. The resulting mixture was poured into a mixture of crashed ice and aqueous $K_2CO_3$ solution. The organic layer was washed with saturated brine, dried over anhydrous $Na_2SO_4$ and concentrated in vacuo to give 2.35 g (54%) as a brown solid. A small portion of the solid was recrystallized with acetone for characterization: mp 68–70° C.; $^1H$ NMR (300 MHz, $CDCl_3$) 8.11 (dd, J=9.3, 6.0 Hz, 1H, Ar—H), 7.57 (dd, J=9.1, 2.5 Hz, 1H, Ar—H), 7.29-7.26 (m, 1H, Ar—H), 3.06 (s br, 2H, $CH_2$), 2.96 (s br, 2H, $CH_2$), 1.92 (t, J=3.3 Hz, 4H, $CH_2CH_2$).

EXAMPLE 3

General Procedure for the Synthesis of 5a–i and 6a–i

To a mixture of 6,9-dihalo-1,2,3,4-tetrahydroacridine (3b or 3c, 1.0 eq), 1,n-diaminoalkane (0.5 eq), phenol (2.0 eq), and NaI (0.025 eq) was heated at 180° C. at oil bath for 1.5–3.5 h. After the reaction mixture was cooled to room temperature, it was diluted with EtOAc and made basic with 10% KOH solution. The organic layer was washed with water, brine, dried over $MgSO_4$ and concentrated in vacuo to remove solvent. The resulting residue was purified on flash chromatography ($CH_2Cl_2$ to $CH_2Cl_2$:MeOH=10:1 as eluents) to afford bistacrines in moderate yields.

EXAMPLE 4

1,2-Bis-(6-chloro)tacrinyl-ethane (5a)

According to the general procedure in Example 3, 3b (0.75 g, 2.99 mmol) and 1,2-diaminoethane (0.11 mL, 1.50 mmol) were condensed for 1.5 h to afford, after flash chromatography ($CH_2Cl_2$ to $CH_2Cl_2$:MeOH=10:1 as eluents), 0.41 g (56%) of an ambor solid: mp 97–99° C.; $R_f$ 0.31 ($CH_2Cl_2$/MeOH/$NH_4OH$=10:1:1); $^1H$ NMR (300 MHz, $CDCl_3$) δ 7.91 (s, 2H, Ar—H), 7.82 (d, J=8.0 Hz, 2H), 7.27 (t, J=8.0 Hz, 2H), 3.75 (s br, 4H, $CH_2CH_2$), 3.02 (t, J=5.2 Hz, 4H, 2 $CH_2$), 2.56 (t, J=5.7 Hz, 4H, 2 $CH_2$), 1.95-1.70 (m, 8H, $2CH_2CH_2$); $^{13}C$ NMR (75 MHz, $CDCl_3$) 160.5, 150.6, 148.4, 134.9, 128.2, 125.5, 124.4, 119.2, 117.9, 50.4, 34.4, 25.2, 23.3, 23.1FABMS (NBA as matrix): m/z $[M+H]^+$ 491.2.

EXAMPLE 5

1,4-Bis-(6-chloro)tacrinyl-butane (5c)

According to the general procedure in Example 3, 3b (0.75 g, 2.99 mmol, 1.0 eq) and 1,4-diaminobutane (0.15 g, 1.50 mmol) were condensed under heat for 2.5 h to afford, after flash chromatography ($CH_2Cl_2$ to $CH_2Cl_2$/MeOH=10:1 as eluents), 0.28 g (54%) of 5c as a deep yellow solid: mp 89–91° C., $^1H$ NMR (300 MHz, $CDCl_3$) δ 7.90 (s, 2H, Ar—H), 7.83 (d, J=9.1 Hz, 2H, Ar—H), 7.26 (d, J=9.0 Hz, 2H, Ar—H), 3.48 (t, J=5.3 Hz, 4H, 2 N—$CH_2$), 3.02 (t, J=5.2 Hz, 4H, 2 $CH_2$), 2.62 (t, J=5.9 Hz, 4H, 2 $CH_2$), 1.90-1.82 (m, 4H, $CH_2CH_2$ ), 1.80-1.70 (s br, 4H, $CH_2CH_2$); FABMS (NBA as matrix): m/z $[M+H]^+$ 519.1.

EXAMPLE 6

1,7-Bis-(6-chloro)tacrinyl-heptane (5f)

According to the general procedure in Example 3, 3b (0.75 g, 2.99 mmol) and 1,7-diaminoheptane (0.20 g, 1.50 mmol) were condensed under heat for 2.5 h to afford, after flash chromatography ($CH_2Cl_2$ to $CH_2Cl_2$/MeOH=10:1 as eluents), 0.47 g (56%) of 5f as an amber oil. $^1H$ NMR (300 MHz, $CDCl_3$) 7.92 (s, 1H, Ar—H), 7.89 (s, 1H, Ar—H), 7.27-7.16 (m, 2H, Ar—H), 6.90-6.84 (m, 2H, Ar—H), 3.53 (t, J=7.1 Hz, 4H, 2 N—$CH_2$), 3.01 (s br, 4H, $2CH_2$), 2.64 (s br, 4H, $2CH_2$), 1.88 (s br, 8H, 2 $CH_2CH_2$), 1.67-1.63 (m, 6H, $CH_2CH_2CH_2$), 1.40-1.20 (m, 4H, $CH_2CH_2$); FABMS (NBA as matrix): m/z $[M+H]^+$ 561.2, HR-FABMS exact mass calcd for $C_{33}H_{39}N_4Cl_2$ $[M+H]^+$ 561.2321, found.

EXAMPLE 7

1,7-Bis-(6-fluoro)tacrinyl heptane (6f)

According to the general procedure in Example 3, 3c (0.5 g, 2.13 mmol) and 1,6 -diaminoheptane (0.15 g, 1.10 mmol) were condensed for 1.5 h to afford, after flash chromatography ($CH_2Cl_2$ to $CH_2Cl_2$/MeOH (10:1) to $CH_2Cl_2$/MeOH/$NH_4OH$ (90:5:5) as eluents), 0.14 g (24%) of 6f as an ambor solid: $^1H$ NMR (300 MHz, $CDCl_3$) δ 7.99 (dd, J=9.6, 6.2 Hz, 2H, Ar—H), 7.58 (dd, J=9.9, 2.2 Hz, 2H, Ar—H), 7.10 (td, J=8.0, 2.4Hz, 2H, Ar—H), 3.53 (t, J=7.1 Hz, 4H, 2 N—CH2), 3.05 (s br, 4H, 2 $CH_2$), 2.66 (s br, 4H, 2 $CH_2$), 1.90 (t, J=3.1 Hz, 8H, 2 $CH_2CH_2$), 1.80-1.60 (m, 4H, $CH_2CH_2$), 1.50-1.20 (m, 6H, $CH_2CH_2CH_2$); FABMS (NBA as matrix): m/z $[M+H]^+$ 529.2.

EXAMPLE 8

1,8-Bis-(6-chloro)tacrinyl-octane (5g)

According to the general procedure, 3b (0.75 g, 2.99 mmol) and 1,8-diaminooctane (0.19 g, 1.50 mmol) were condensed under heat for 2 h to afford, after flash chromatography ($CH_2Cl_2$ to $CH_2Cl_2$/MeOH=10:1 as eluents), 0.40 g (46%) of 5g as an amber oil. $^1H$ NMR (300 MHz, $CDCl_3$) 7.86-7.89 (m, 2H, Ar—H), 7.24-7.21 (m, 2H, Ar—H), 6.91-6.74 (m, 2H, Ar—H), 4.01 (s br, 1H, NH), 3.50-3.45 (t, J=7.1 Hz, 4H, 2 N—$CH_2$), 3.10 (s br, 4H, 2 $CH_2$), 2.63 (s br, 4H, 2 $CH_2$), 1.89 (s br, 8H, 2 $CH_2CH_2$), 1.64-1.50 (m, 4H, $CH_2CH_2$),1.43-1.20 (m, 8H, 2 $CH_2CH_2$); FABMS (NBA as matrix): m/z $[M+H]^+$ 575.2, HR-FABMS exact mass calcd for $C_{34}H_{41}N_4Cl_2$ $[M+H]^+$ 575.2 found.

EXAMPLE 9

1,8-Bis-(6-fluoro)tacrinyl octane (6g)

According to the general procedure, 3c (0.4 g, 1.70 mmol) and 1,6-diaminooctane (0.13 g, 0.90 mmol) were condensed for 1.5 h to afford, after flash chromatography ($CH_2Cl_2$ to $CH_2Cl_2$/MeOH (10:1) to $CH_2Cl_2$/MeOH/$NH_4OH$ (90:5:5) as eluents), 0.15 g (32%) of 6g as an ambor solid: $^1$H NMR (300 MHz, $CDCl_3$) δ 7.97 (dd, J=9.1, 6.1 Hz, 2H, Ar—H), 7.55 (dd, J=10.4, 2.5 Hz, 2, Ar—H), 7.09 (td, J=7.3, 2.5 Hz, 2H, Ar—H), 3.50 (t, J=6.9 Hz, 4I, (2 N—$CH_2$), 3.02 (s br, 4H, 2 $CH_2$), 2,65 (s br, 4H, 2 $CH_2$), 1.89 (t, J=3.0 Hz, 8H, 2 $CH_2CH_2$), 1.65 (t, J=6.9 Hz, 4H, $CH_2CH_2$), 1.50-1.20 (m, 8H, $CH_2CH_2CH_2$); FABMS (NBA as matrix): m/z [M+H]$^+$ 543.2.

EXAMPLE 10

1,10-Bis-(6-chloro)tacrinyl-decane (5i)

According to the general procedure, 3 (0.75 g, 2.99 mmol) and 1,10-diaminodecane (0.26 g, 1.50 mmol) were condensed under heat for 2 h to afford, after flash chromatography ($CH_2Cl_2$ to $CH_2Cl_2$/MeOH=10:1 as eluents), 0.38 g (42%) of 5i as an amber oil. $^1$H NMR (300 MHz, $CDCl_3$) 8.00-7.86 (m, 4H, Ar—H), 7.23-7.20 (m, 2H, Ar—H), 3.46 (s br, 4H, 2 N—$CH_2$), 3.00 (s br, 4H, 2 $CH_2$), 2.63 (s br, 4H, 2 $CH_2$), 1.88 (s br, 8H, 2 $CH_2CH_2$), 1.70-1.50 (m, 4H, $CH_2CH_2$), 1.50-1.10 (m, 12H, 3 $CH_2CH_2$); FABMS (NBA as matrix): m/z [M+H]$^+$ 603.3.

EXAMPLE 11

1,4-Bis-[(6-chloro-tacrinyl)methyl]-cyclohexane (7b)

According to the general procedure, 3b (0.78 g, 3.1 mmol) and 1,4-bis(aminomethyl)cyclohexane (0.22 mL, 1.55 mmol) were condensed under heat for 2.5 h to afford, after flash chromatography ($CH_2Cl_2$ to $CH_2Cl_2$/MeOH=10:1 as eluents), 0.52 g (58%) of 7b as a golden glass foam. mp 93–95° C.; $^1$H NMR (300 MHz, $CDCl_3$) δ 7.88 (s, 2H, Ar—H), 7.86 (d, J=8.3 Hz, 2H, Ar—H), 7.25 (d, J=8.1 Hz, 2H, Ar—H), 4.05 (s br, 2H, 2 NH), 3.55-3.30 (m, 4H, 2 N—$CH_2$), 3.01 (s br, 4H, 2$CH_2$), 2.63 (s br, 4H, 2$CH_2$), 1.88 (s br, 8H, 2 $CH_2CH_2$), 1.65 (2 br, 4H, 2 $CH_2$), 1.41 (s br, 4H, 2 $CH_2$); FABMS (NBA as matrix): m/z [M+H]$^+$ 573.2.

EXAMPLE 12

1,4-Bis-[(6-fluoro-tacrinyl)methyl]-cyclohexane (7c). According to the general procedure, 3c (0.27 g, 1.15 mmol) and 1,4-bis(aminomethyl)-cyclohexane (0.09 mL, 0.62 mmol) were condensed under heat for 1.5 h to afford, after flash chromatography ($CH_2Cl_2$ to $CH_2Cl_2$/MeOH=10:1 as eluents), 70 mg (21%) of 7c as a golden glass foam. $^1$H NMR (300 MHz, $CDCl_3$) δ7.93 (dd, J=9.1, 5.8 Hz, 2H, Ar—H), 7.50 (dd, J=10.0, 2.5 Hz, 2H, Ar—H), 7.09 (td, J=6.8, 2.6 Hz, 2H, Ar—H), 3.60 (m, 2H, 2 C-H), 3.55-3.30 (m, 4H, 2 N—$CH_2$), 3.02 (s br, 4H, 2 $CH_2$), 2.70-2.55 (m, 4H, 2 $CH_2$), 2.00-1.75 (m, 8H, 2 $CH_2CH_2$), 1.70-1.40 (m, 8H, 2 $CH_2CH_2$); FABMS (NBA as matrix): m/z [M+H]$^+$ 541.2.

EXAMPLE 13

N-[2-(3-indolyl)ethyl]-6-chlorotacrine (8b)

Compound 3 (0.75 g, 2.99 mmol) and tryptamine (0.48g, 2.99 mmol) were condensed for 2 h to afford, after flash chromatography ($CH_2Cl_2$ to $CH_2Cl_2$/MeOH=10:1 as eluents), 0.73 g (65%) of 8b as an amber solid: mp 79–81° C., $^1$H NMR (300 MHz, $CDCl_3$) 9.20 (s, 1H, NH), 7.90 (s, 1H, Ar—H), 7.82 (d, J=6.5 Hz, 1H, Ar—H), 7.62 (d, J=6.2 Hz, 1H, Ar—H), 7.36 (d, J=5.2 Hz, 1H, Ar—H), 7.25-7.15 (m, 3H, Ar—H), 7.02 (s, 1H, Ar—H), 4.27 (s br, 1H, NH), 3.86 (s br, 2H, $CH_2$), 3.86 (s br, 2H, $CH_2$), 3.13 (t, J=5.6 Hz, 2H, $CH_2$), 2.98 (t, J=5.2 Hz, 2H, $CH_2$), 2.38 (t, J=6.2 Hz, 2H, $CH_2$), 1.90-1.60 (m, 4H, $CH_2CH_2$); EIMS (70 eV) m/z: 375 (M$^+$, 10), 377 (M+2$^+$, 3.3).

The tacrine derivative in this invention may be administered in a convenient chemical or physical form. The tacrine derivative or its salt may be administered to a patient suffering from Alzheimer disease orally or by subcutaneous or intravenous, injeciton, or intracerebroventricularly by means of an implanted reservoir.

The tacrine derivative and its pharmaceutically acceptable salts are generally sparingly soluble in water at room temperature. Therefore, it may be formulated in the form of an aqueous solution or suspension. Typically, such a solution or suspension will be formulated at a concentration of 0.1–50 mg/mL, more commonly 5–40 mg/mL. When parenterally administering said tacrine derivative or its salt, typical dosage rates are in the range of 0.25–1,000 mg per day depending upon the patient. Preferred dosage rates are in the range of 1–250 mg per day depending upon the patient. In preparing an injectable form, standard pharmaceutical techniques may be used.

The tacrine derivative or it pharmaceutically acceptable salts may also be administered orally in liquid or solid dosage forms, such as an aqueous suspension, a solution in aqueous ethanol, a tablet, or a capsule. Higher dosage may be used when administered orally. For example, dosages in the range of 0.5–2,000 mg may be used depending upon the patient. Preferred dosage rates are in the range of 2–500 mg per day depending upon the patient. In preparing an oral dosage form, standard techniques may be used. Of course, it should be understood that the dosage ranges listed above are exemplary and those of skill in the art will be able to use higher and lower dosages. Also it should be noted that specific doses within these ranges are particularly contemplated such as 0.5 mg/day, 1 mg/day; 2 mg/day; 4 mg/day; 8 mg/day 10 mg/day; 15 mg/day; 20 mg/day; 30 mg/day; 40 mg/day; 50 mg/day; 100 mg/day; 150 mg/day; 200 mg/day; 250 mg/day; 300 mg/day; 350 mg/day; 400 mg/day; 450 mg/day; 500 mg/day; 600 mg/day; 700 mg/day etc. This dosages may be administered in a single dose or multiple daily doses.

If desired, a pharmaceutically acceptable excipient, such as lactose or buffer, may be used in preparing a suitable dosage form of said tacrine derivative or its salts.

If desired, a sustained/controlled release dosage form may be made, which releases the active ingredient over a period of time thereby maintaining a controlled level of said tacrine derivative or its salts in a patient. The sustained/controlled rlease dosage form may be made by standard pharmaceutical techniques for preparing sustained/controlled dosage forms.

If desired, said tacrine derivative or it pharmaceutically acceptable salts may be administered in combination with other drugs for Alzheimer's disease, such as galanthamine or its salt.

Ramification and Scope

In conclusion, this invention comprises a series of tacrine derivatives, the preparation, and the methods for treating Alzheimer's diesease by said tacrine derivatives. Although the description above contains many specificities, these should not be construed as limiting the scope of the invention but as merely providing the illustrations of some of the presently preferred embodiments of this invention.

Thus, the scope of this invention should be determined by the appended claims and their legal equivalents, rather by the examples given,

What is claimed is:

1. A compound having a formula as shown in the following structure or its salt:

(a)
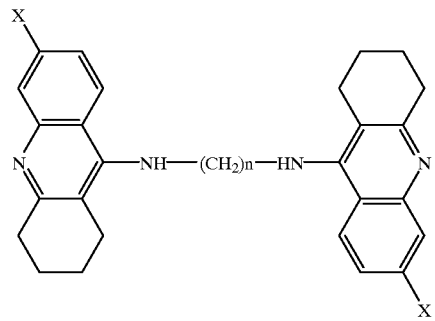

wherein n is an integer between 2 and 10, X is defined as Cl or F;

(b)
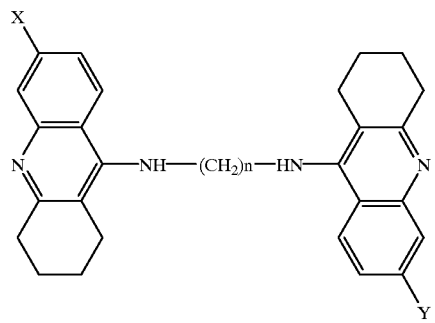

wherein n is an integer between 2 and 10, X is defined as H, Cl, F and Y is defined as H, Cl, F but X is not the same as Y (c)
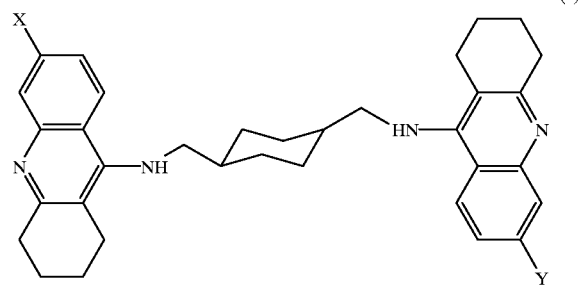

wherein X is H, Cl, F and Y is H, Cl, F and (d)
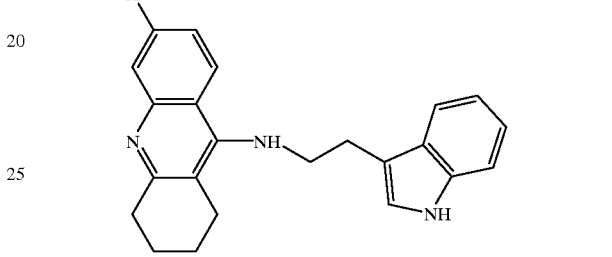

wherein X=H, Cl, F.

2. A method of treating Alzheimer's disease and related dementia which comprises administering to a patient having such as disease a therapeutically effective amount of the compound in claim 1.

3. A method according to claim 2, wherein the administration is parenteral at a daily dosage of between about 0.25 mg to about 1,000 mg.

4. A method according to claim 2, wherein the administering is at a dosage rate of between about 1 mg to about 250 mg per day.

5. A method according to claim 2, wherein the administration is oral and is in the range of between about 0.5 mg to about 2,000 mg per day.

6. A method according to claim 2, wherein the said dosage rate is between about 2 mg to about 500 mg per day.

7. A method according to claim 2, wherein the administration is via an implanted reservoir.

8. A method of treating Alzheimer's disease, which comprises administering to a patient a therapeutically effective amount of the compound in claim 1 in combination with galanthamine or its salt.

* * * * *